(12) United States Patent
Shaw

(10) Patent No.: US 12,017,513 B2
(45) Date of Patent: Jun. 25, 2024

(54) HAND SANITIZER, AIR PURIFICATION, AND FOGGER VEHICLE MOUNT

(71) Applicant: Al Farentino Shaw, Westampton, NJ (US)

(72) Inventor: Al Farentino Shaw, Westampton, NJ (US)

( * ) Notice: Subject to any disclaimer, the term of this patent is extended or adjusted under 35 U.S.C. 154(b) by 492 days.

(21) Appl. No.: 17/246,158

(22) Filed: Apr. 30, 2021

(65) Prior Publication Data

US 2022/0080811 A1 Mar. 17, 2022

Related U.S. Application Data

(60) Provisional application No. 63/079,800, filed on Sep. 17, 2020.

(51) Int. Cl.
| | |
|---|---|
| *B60H 3/00* | (2006.01) |
| *A61L 2/16* | (2006.01) |
| *A61L 9/12* | (2006.01) |
| *B60R 11/00* | (2006.01) |

(52) U.S. Cl.
CPC ............ *B60H 3/0014* (2013.01); *A61L 2/16* (2013.01); *A61L 9/12* (2013.01); *B60H 3/0035* (2013.01); *B60H 3/0078* (2013.01); *A61L 2202/16* (2013.01); *B60H 2003/0042* (2013.01); *B60R 2011/0005* (2013.01); *B60R 2011/0056* (2013.01); *B60R 2011/0085* (2013.01)

(58) Field of Classification Search
CPC ..... A61L 9/12; A61L 9/20; A61L 2/16; A61L 2/10; A61L 2209/111; A61L 2209/13; A61L 2209/15; B60H 3/0014; B60H 3/0035; B60H 3/0078; B60H 2003/0042; B60R 11/00; B60R 2011/0005; B60R 2011/0056; B60R 2011/0085
See application file for complete search history.

(56) References Cited

U.S. PATENT DOCUMENTS

| | | | |
|---|---|---|---|
| 4,105,246 | A | 8/1978 | Trumbull |
| 5,099,182 | A | 3/1992 | Isaacson et al. |
| 5,779,205 | A | 7/1998 | Ching |

(Continued)

OTHER PUBLICATIONS

Dropi, Dropi Touchless Sanitizer Dispenser, Apr. 28, 2021 at https://mydropi.com.

*Primary Examiner* — Lessanework Seifu
(74) *Attorney, Agent, or Firm* — Michael Huey, Esq.; Law Office of Michael Huey

(57) ABSTRACT

The present invention is a hand sanitizer, air purification, fogger vehicle mount, or combination thereof, attach to a dashboard of a vehicle. Its purpose is to maximize disinfecting opportunities as a countermeasure to the spread of disease, including COVID-19. As a hand sanitizer, this invention is a hand-free device that minimizes cross-contamination among vehicle patrons during operation. A sensor, activated by hand proximity, sends a signal to a controller, then to a pump to dispense a portion-controlled volume of hand sanitizer. To disinfect airborne antigens, HEPA filtration and UV light are utilized. Pathogen lingering on surfaces are disinfected by a fogger, which dispenses atomized droplets throughout a vehicle. To eliminate exposure to nebulized sanitizer, the controller may receive a wireless signal from outside the vehicle. Independently powered, a vehicle can be sanitized each time it arrives at a destination, made ready to transport the next group of patrons safely.

31 Claims, 9 Drawing Sheets

(56) References Cited

U.S. PATENT DOCUMENTS

| | | | |
|---|---|---|---|
| 5,979,724 | A | 11/1999 | Loewenthal, Jr. et al. |
| 5,992,807 | A | 11/1999 | Tarulli |
| 6,048,265 | A | 4/2000 | Apple |
| 6,305,656 | B1 | 10/2001 | Wemyss |
| 6,888,940 | B1 | 5/2005 | Deppen |
| 7,021,593 | B1 | 4/2006 | Fan |
| 7,296,771 | B2 | 11/2007 | Kalis et al. |
| 8,061,670 | B1 | 11/2011 | White |
| 8,602,257 | B2 | 12/2013 | Godsell |
| 8,608,032 | B2 | 12/2013 | Wolosuk |
| 9,060,655 | B2 | 6/2015 | Iseri et al. |
| 9,271,611 | B2 | 3/2016 | Stratmann |
| 9,271,612 | B2 | 3/2016 | Miller |
| 9,532,566 | B1 | 1/2017 | Dunklau et al. |
| 9,573,531 | B2 | 2/2017 | Zhang |
| 9,758,101 | B2 | 9/2017 | Clair-Chalupka |
| 10,028,497 | B1 | 7/2018 | Brookins |
| 10,348,877 | B1 | 7/2019 | Von Borstel et al. |
| 10,499,774 | B1 | 12/2019 | Ryan et al. |
| 10,799,839 | B1 | 10/2020 | Brookins |
| 2013/0262345 | A1 | 10/2013 | Ciavarella et al. |

HAND SANITIZER, AIR PURIFICATION, AND FOGGER VEHICLE MOUNT

CROSS REFERENCE TO RELATED APPLICATIONS

This application is related to and claims priority from U.S. Provisional Patent Application No. 63/079,800 filed on Sep. 17, 2020 by Al Shaw entitled "Hand Sanitizer Vehicle Mount" the contents of which are hereby incorporated by reference.

FIELD OF INVENTION

The present invention relates to a hand sanitizer, air purification, fogger, or combination thereof, mounted to a vehicle dashboard.

BACKGROUND OF THE INVENTION

The present invention is a hand sanitizer, air purification, fogger vehicle mount, or combination thereof, addressing the need to disinfect a person's hand immediately after leaving a retail store, school, or other public establishments, where infections are most prominent. Recently, the life-threatening pathogen COVID-19 has taken more than 500,000 lives in the Unites States and 3,000,000 lives globally. While other hand sanitizers exist, they are dispensed manually, requiring a person to handle a bottle or press the top of a pump, previously touched by unsterilized hands. Consequently, a person may ironically become infected by handling the very bottle designed to prevent infection.

To make matters worse, in most cases, a person must wait until reaching a rest room of one's home or office to gain access to hand sanitizers. All the while, spreading potential pathogens to ingress, egress, or other points of entry of building, subjecting that person and others to cross-contamination numerous times before hand sanitizers are available. The particularly vulnerable population, including elderly population, that relies on shared transportation is in a category of people more susceptible to suffer illness or death.

The recent COVID-19 pandemic has taught us that hand sanitation is not enough. Viruses and bacteria can infect others as airborne or surface particles. Therefore, face masks must be worn and packages must be quarantined. Consequently, infection rate reduction requires more than hand sanitation. The air must be purified and surfaces must be disinfected. This invention provides an effective mean to disinfect a person's hands, vehicle's air compartment, and vehicle surfaces (e.g., seats, dashboard, steering wheel), all within in a single device, which currently does not exist.

Other inventors have recognized that enhancing opportunities for improve hygiene minimizes the spread of germs, viruses, or bacteria. However, their inventions operate through substantially different means. Recent trends in hand sanitation have been focused on enforcing compliance through reminder and identification of employees who use, or don't use, hand sanitizer before exiting a room.

In 2013, Godsell was issued a patent for a "Multifunctional Hand Sanitizer Device" (U.S. Pat. No. 8,602,257). Godsell's invention is a vehicle cup holder that dispenses a combination of hand sanitizer and hand wipes. It has no automated circuitry; therefore, not a hands-free device that prevents cross-contamination by merely using the device. Furthermore, it does not describe any means to disinfect airborne antigens.

In 2015, Iseri et al. were issued a patent for a "Dispenser for Hand Sanitizer" (U.S. Pat. No. 9,060,655). This is a wall mounted hand sanitizer dispenser. The point of novelty is the presence of a push plate, which communicates a signal to dispense hand sanitizer and records the identity of the person utilizing the device. The user information is then transmitted to a networked server. The purpose is to ensure hygiene compliance of hospital and health care employees. Thus, the objective of this invention is different from the present invention. Furthermore, because the user must touch the push plate, it is not a hands-free device. In addition, it is neither an air purification device nor a fogger.

In 2016, Stratmann was issued a patent for a "Systems for Improving Hand Hygiene" (U.S. Pat. No. 9,271,611). The purpose of this invention is to improve hygiene compliance by reminding people exiting a room to use hand sanitizer. Hence, this device is mounted on a wall beside a door, rather than a vehicle. While depicted as a wired-device, the written disclose describes a wireless hands-free device with two proximity sensors: (i) to detect the location of person in a room, and (ii) to detect the location of a person's hands under the dispensing spout. Furthermore, the information is wirelessly transmitted to a network server. Similar to the previous patent, the objective is to improve hygiene compliance, which is different from the present invention that uses wireless technology to dispense sanitizer, and to activate or deactivate the fogger.

In 2017, Clair-Chalupka was issued a patent for a "Hand Sanitizer for Vehicles" (U.S. Pat. No. 9,758,101). This hand sanitizer dispenser is mounted within a rear-view mirror for a vehicle, unlike the present invention that is more conveniently located on the dashboard. This enables the present invention to run a reservoir tube to a larger external reservoir to supply sanitizer, without obstructing a driver's view of the road. Furthermore, the present invention includes numerous additional elements, including a HEPA filtration, UV lamp, and fogger assembly to kill airborne and surface antigens.

In 2019, Ryan et al. were issued a patent for a "Liquid Dispenser" (U.S. Pat. No. 10,499,774). This is a vehicle cup holder that dispenses hand sanitizer. Unlike Godsell's cup holder invented in 2013, this cup holder has a receptacle cap that captures spilled liquid into a collection pool. The remaining elements are similar to Godsell's patent, wherein the receptacle cap is depressed to pump hand sanitizer from a reservoir through a discharge port to dispense hand sanitizer.

Through the years, patents have issued for GPS and cell phone vehicle mounts, but none of these patents disclose a hand sanitizer, air purification, and fogger vehicle mount. For example, in 1978, Trumbull was issued a patent for a "Multi-Purpose Dashboard Attachment" (U.S. Pat. No. 4,105,246). This patent is over 40 years old and among the first attempts to mount something to a vehicle dashboard. Essentially, the inventor uses brackets to mount a shallow drawer to the dashboard.

In 1998, Ching was issued a patent for an "Extensible Windshield Portable Phone Holder" (U.S. Pat. No. 5,779, 205). The inventor uses a suction cup to attach a phone holder to a windshield. The device has a rotatable and extendable arm to position the mount above the dashboard, based on the driver's preference. In 1999, Loewenthal, Jr. et al. were issued a patent for an "Automobile Universal Dashboard Mounting Apparatus" (U.S. Pat. No. 5,979,724). The patent discloses its use to hold personal devices (e.g., cell phones and walkie talkies) by attaching them to a vehicle vent. It has two cable tie-like straps that hooks around the rib of a vent grill. A locking mechanism then secures a bracket to the vent. This supports a rotatable carrier or bucket to hold the personal device. That same year, in 1999, Tarulli was issued a patent for a "Universal Magnetic Stand for Cell Phones" (U.S. Pat. No. 5,992,807). The concept is similar to Loewenthal, Jr. et al., but utilizes a magnet to attach a bracket to the dash board. This device is less sophisticated and non-rotatable, but certainly less expensive to make.

In 2001, Wemyss was issued a patent for a "Magnetic Coupler and Various Embodiments Thereof" (U.S. Pat. No. 6,305,656). This invention also uses magnets like the Tarulli patent above; however, instead of securing a bracket to a dashboard, it secures a holding device to a cup holder. The holding device is designed to secure a radar detector, hand held computer, calculator, cell phone, etc. In 2005, Deppen was issued a patent for a "Magnetic Holder for Cell Phones and the Like" (U.S. Pat. No. 6,888,940). This invention is also a magnetic holder, but the point of novelty is the attachment of the magnet to the face of the dashboard.

In 2006, Fan was issued a patent for a "Vacuum Suction Apparatus" (U.S. Pat. No. 7,021,593). This invention is an improvement upon the existing vacuum suction design by including a cogwheel fixed above the receptacle with a lever to manually adjust the suction strength. In 2007, Kalis et al. were issued a patent for a "Separable Ball and Socket Assembly for Electronic Device Mounts" (U.S. Pat. No. 7,296,771). The point of novelty is the use of a ball and socket joint, rather than the flexible stem of Fan's invention. The ball and socket joint offer more flexibility and stability to the secured device. In 2011, White was issued a patent for a "Cup Holder Adapter for Mounting Portable Electronic Devices in a Vehicle Console" (U.S. Pat. No. 8,061,670). This invention is a cup holder that utilizes a suction cup to secure the electronic device.

In 2017, Zhang was issued a patent for a "Mounting Apparatus for Portable Electronic Device" (U.S. Pat. No. 9,573,531). This device combines the use of a removable suction cup, pivoting arm, and magnets. In 2019, Von Borstel et al. were issued a patent for a "Smartphone Dashboard Mount Assembly" (U.S. Pat. No. 10,348,877). Notwithstanding all the improvements through the years, nobody filed a patent to use Velcro to secure a dashboard mount. Functionally, there is probably little significant difference in overall cost, but the application of Velcro was an overlooked and nonobvious way to secure a dashboard mount; therefore, patentable.

Regarding foggers, the evolution of this technology has been focused on making the device more portable to dispense smoke or insecticide, rather than hand sanitizer. For example, in 1992, Isaacson et al. were issued a patent for a "Brushless DC Motor Powered Fogging Apparatus" (U.S. Pat. No. 5,099,182). It operates with a 12-volt power supply and delivers 0.2 horsepower at 28,000 rpm. The 1.6-inch diameter motor with rotating rings of porous ceramic material atomizes liquid, then dispenses it. The invention is focused on engineering a fogger, without disclosing any particular application.

In 2000, Apple was issued a patent for a "Aerosol Dispenser for Use in a Vehicle" (U.S. Pat. No. 6,048,265). The inventor uses an aerosol dispensing unit that release odor neutralizing agent by spraying or fogging. The aerosol composition is circulated through the car's air circulation system by placing a portable fogger near the car's air intake vent. In other words, it does not disclose any independent air purification system, but rather uses the vehicles' existing ventilation system. Consequently, HEPA filtration or UV light technology to eliminate upward of 99.97% of air particles and pathogens down to 0.3-micron size is not disclosed, and unlikely achievable by Apple's invention. Furthermore, it neither dispenses hand sanitizer as a hands-free device nor does it operate with an independent power source; therefore, ineffective when the vehicle ventilation system is not running.

In 2013, Wolosuk was issued a patent for a "Dispenser" (U.S. Pat. No. 8,608,032). The dispenser holds a disinfectant propellant container. The carriage is pivotally mounted to a rotating assembly, actuated by a motor, and connected to a power source (e.g., battery). While this fogger uses a mount, its function of rotating a can of propellant (e.g., insecticide) operates quite differently from the present invention. In 2017, Dunklau et al. were issued a patent for a "Ultra Low Volume Fogger" (U.S. Pat. No. 9,532,566). Unlike the previous foggers that utilize spinning porous rotors as speeds upward of 30,000 rpm, this device uses a nozzle to create fog and a fan to push the fog through a tube.

In 2018, Brookins was issued a patent for a "Misting System" (U.S. Pat. No. 10,028,497). The novelty is the creation of a portable system with interior housing, electrical compartment, lid assembly, and outlet. The lid assembly has locking tabs and a handle to facilitate transport. In 2020, Brookins was issued a patent for a "Multifunctional Misting System" (U.S. Pat. No. 10,799,839). This invention was made by the same inventor of the above patent "Misting System." It adds a porous housing, mist blower assembly, valve assembly, control panel assembly, pump-motor assembly, and a tank assembly. The motor is powered by a battery attached to a motor-battery bracket. The portable mister is designed to spray insecticide in a mobile fashion, rather than fogging the inside of a vehicle. There is no disclose of any hand sanitizer element, hands-free technology, or air purification mechanisms.

SUMMARY OF THE INVENTION

While the concepts of a hand sanitizer, air purification, fogger or vehicle mount exist independently, these features have never been combined together into a single device to create a synergistic technological advancement, namely a convenient and complete vehicle sanitation system. The recent COVID-19 pandemic has taught us that we are ill equipped to deal with infectious disease or viruses. To minimize exposure to infectious or lethal pathogens, disinfecting areas that harbor such pathogens minimizes the risk of exposure to friends and family. A key area of potential expose is inside a vehicle, where everyone is within 6 feet from each other.

This invention solves existing problems by providing access to hand sanitizer inside a vehicle, enabling a person to have clean hands while inside a vehicle, and prior to entering a home or public establishment. Because this invention is a hand-free device, utilizing a sensor to detect the proximity of a person's hands to the dispenser, the potential of operational cross-contamination is eliminated.

Pathogens reside not only on a person's hands, but also on surfaces that may recontamination a person's hands after they have been sanitized. Therefore, this device is also a fogger that disperses sanitizer into the air, ultimately settling onto vehicle surfaces, leaving a homogenous layer of disinfectant. Sanitizer inside a refillable cartridge is moved through a pump, which creates fluid pressure and pushes the sanitizer through a nozzle to create atomized or nebulized droplets. The nozzle is a misting nozzle or a spraying nozzle. In a preferred embodiment, a fogging nozzle is utilized, because smaller droplet size creates a more homogenous dispersion of sanitizer in the air and layer of sanitizer on the surfaces of the vehicle.

Because patrons want to avoid inhalation of sanitizer, the dispenser has a wireless controller that can activate or deactivate the dispenser from a remote device, such as a cell phone, tablet, or Wi-Fi network. A person (e.g., soccer mom) may transport multiple groups of people during a busy day. With this device, the vehicle surfaces may be sanitized every time the vehicle reaches a destination, ready to transport the next group of patrons safely.

Vehicles have air filtration systems, but car maintenance or service stations are not likely to install a HEPA filter due to added costs. Furthermore, vehicle ventilation systems are typically only air filtration system, not air purification systems. Specifically, vehicles do not use germicidal UV light to disinfect the air. This invention provides an air purification system, utilizing HEPA filtration technology and UV light that may remove 99.97% of airborne particles, including dust mites, pollen, pet dander, mold, bacterial, staph, influenza, rhinovirus, and other pathogens inside a vehicle. Unlike a vehicle air filtration system, which is turned off with the vehicle, this invention can continuously clean the air while the vehicle is turned off, because it contains an independent power source (i.e., a battery). In a preferred embodiment, the battery is rechargeable through a power adapter socket, which connects to a vehicle cigarette lighter socket. Consequently, both the air and surfaces of the vehicle can be disinfected each time a vehicle reaches its destination.

The dispenser is attached to a pivoting or rotatable arm, so the device is ergonomically friendly and does not obstruct a driver's view of the road through a windshield. The invention is secured to a base, which is removably attached to a dashboard of a vehicle. There are many known ways to secure a mount, including adhesives, Velcro, or magnets. In a preferred embodiment, a suction cup with a lever is utilized to facilitate shared usage among multiple vehicles. Specifically, the lever modifies the pressure under the suction cup to either form a tight seal or release the device from the dashboard, which is preferred over permanent adhesives.

This invention is designed to be portable; therefore, holds a small quantity of sanitizer stored inside a refillable cartridge. To change a refillable cartridge of sanitizer, actuating a mount lock enables the refillable cartridge to slide along rails and exit the dispenser. The dispenser is now ready to receive a new refillable cartridge. Because the refillable cartridge has limited capacity, it has the option to connect to an external reservoir stored in a dashboard compartment, kick panel, or other storage areas within a vehicle. The reservoir averts frequent changes of the refillable cartridge for active family members. Tube anchors facilitate cable or tube management, so the overall invention is sleek and ergonomically conscious, as it advances public safety.

BRIEF DESCRIPTION OF THE INVENTION

The embodiments set forth in the figures of the accompanying drawings are illustrated by way of examples, and not by way of limitations. While the claims distinctly point out the present invention, the following drawings and descriptions taken in conjunction aids in the understanding of the invention:

DETAILED DESCRIPTION OF THE INVENTION

Figure 1:
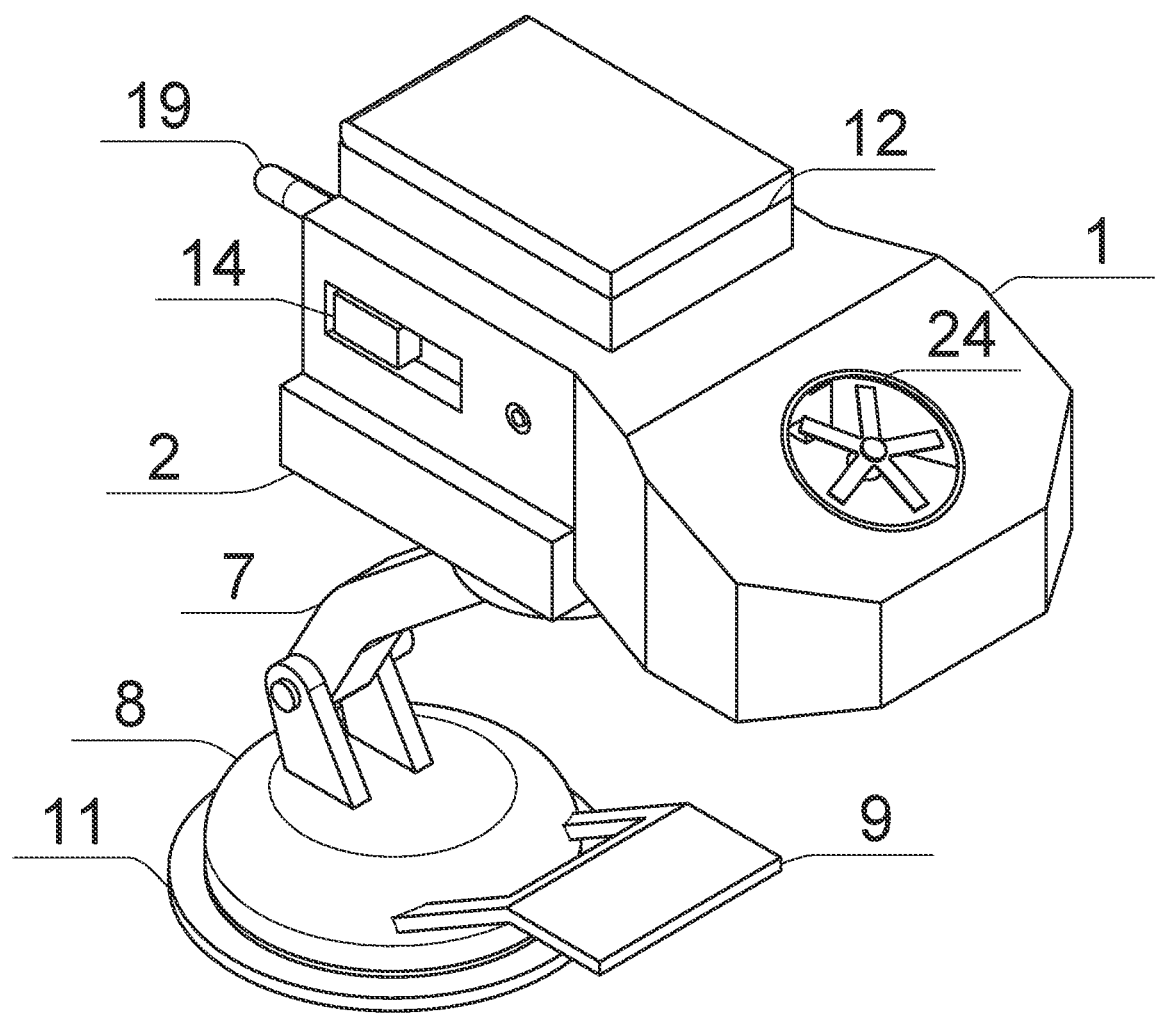
FIG. 1 is a perspective view of a hand sanitizer, air purification, and fogger vehicle mount.
Figure 2:
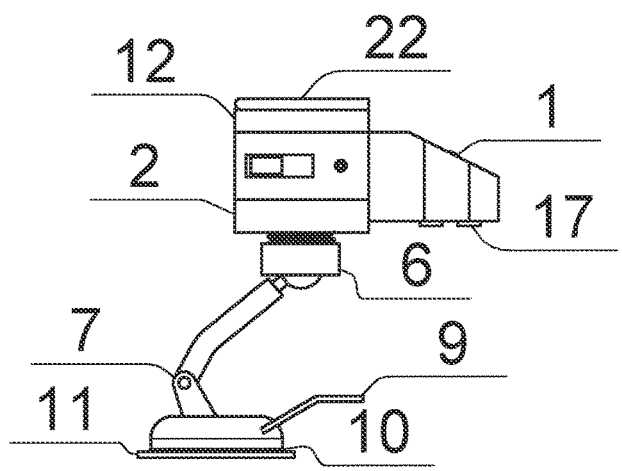
FIG. 2 is a side view of a hand sanitizer, air purification, and fogger vehicle mount.
Figure 3:
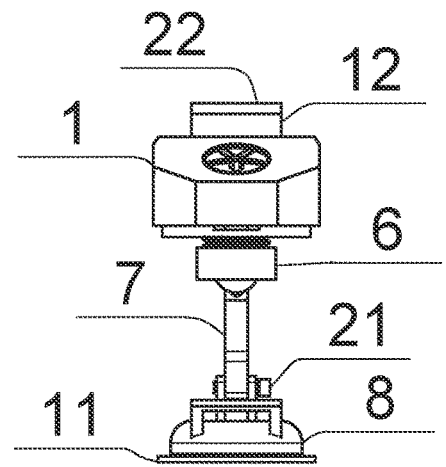
FIG. 3 is a front view of a hand sanitizer, air purification, and fogger vehicle mount.
Figure 4:
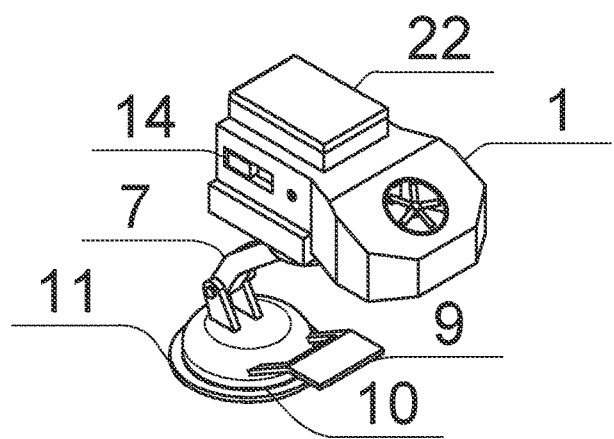
FIG. 4 is north east perspective view of a hand sanitizer, air purification, and fogger vehicle mount.
Figure 5:
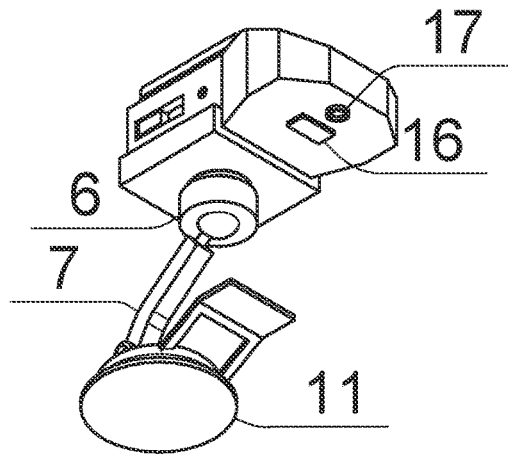
FIG. 5 is south east perspective view of a hand sanitizer, air purification, and fogger vehicle mount.
Figure 6:
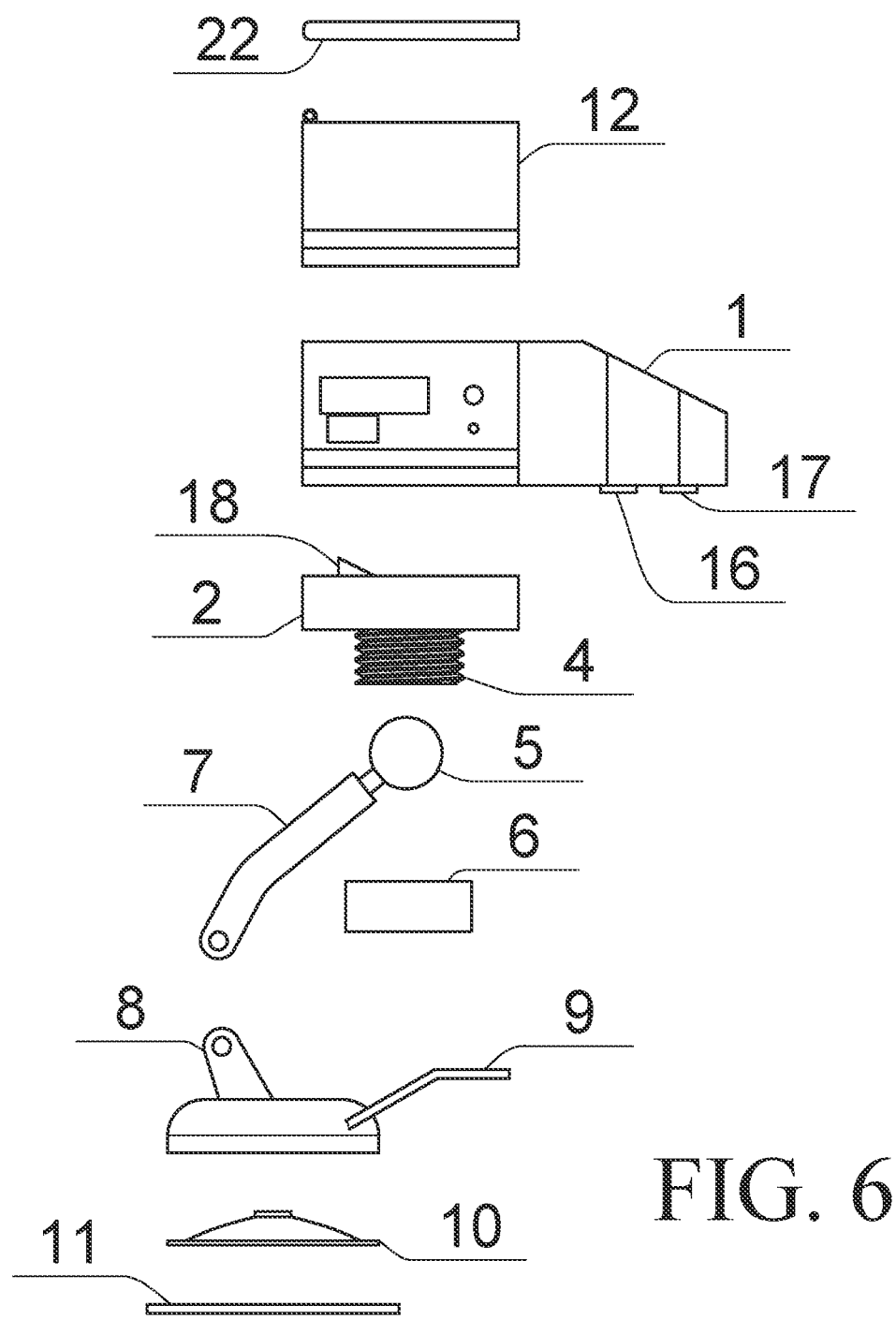
FIG. 6 is an exploded view of the invention.
Figure 7:
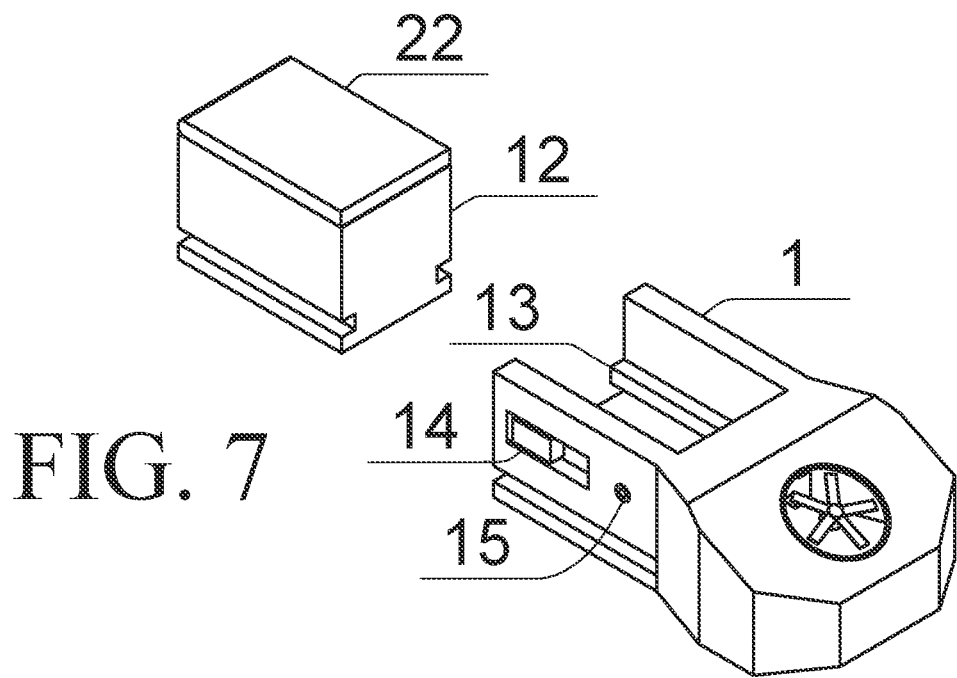
FIG. 7 depicts the refill cartridge with slots that correspond with the refill cartridge rails of a dispenser.
Figure 8:
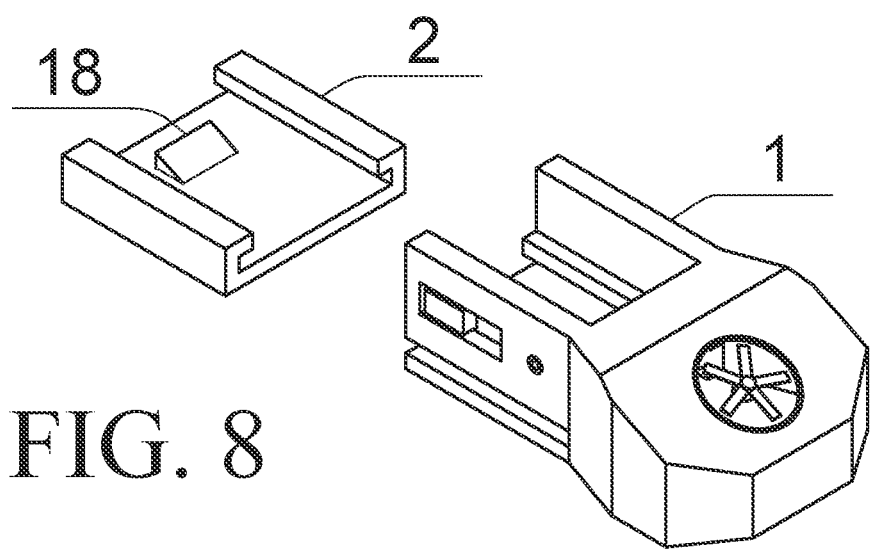
FIG. 8 depicts a mount comprising a mount lock that secures a dispenser to a mount.

The present invention is a hand sanitizer, air purification, fogger vehicle mount, or combination thereof. Its ergonomic design, such as customizable height and direction adjustments, gives vehicle patrons ample space to place one's hands under the dispenser. A rotatable arm enables the dispenser to rotate to face a driver or passenger in a vehicle. Meanwhile, selecting a maximum height that does not obstruct a driver's view furthers safe driving practices. The compact and sleek design compliments the contour of a vehicle, while a refill cartridge makes reloading the dispenser an easy operation.

The invention comprises of a dispenser 1 with a bottom wall that houses a sensor 16 and spout 17. The sensor 16 is motion activated, designed to send a signal to a pump 26, which in turn delivers a preset volume of hand sanitizer.

The dispenser 1 has a power switch 14 to activate or deactivate the pump 26. In a preferred embodiment, the dispenser 1 is powered by rechargeable batteries 30. A power adapter socket 15 is affixed to a side wall of the dispenser 1, facilitating recharge of the batteries.

Figure 9:
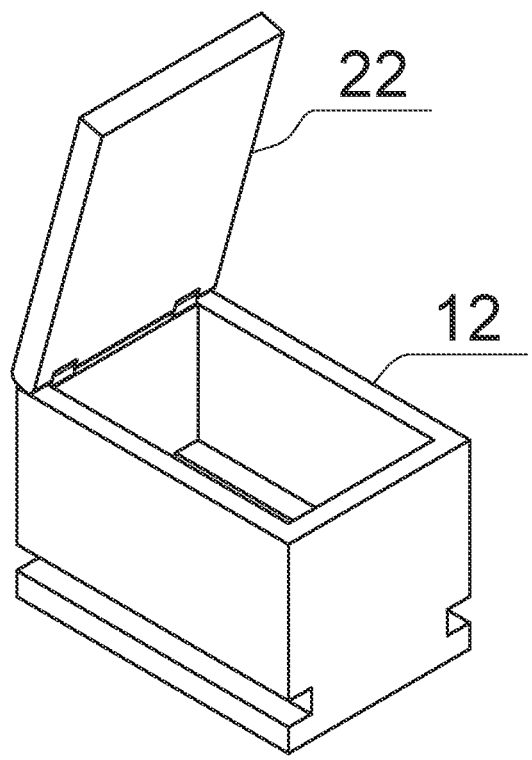
FIG. 9 and FIG. 10 illustrate a refill cartridge lid in an open or closed configuration, respectively.
Figure 10:
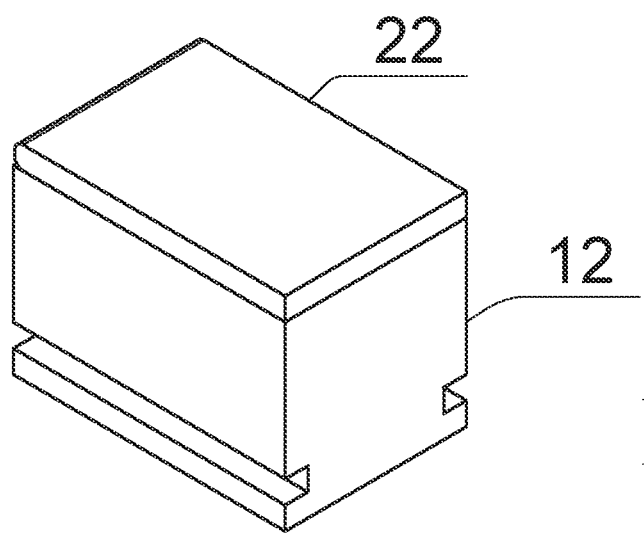
Figure 11:
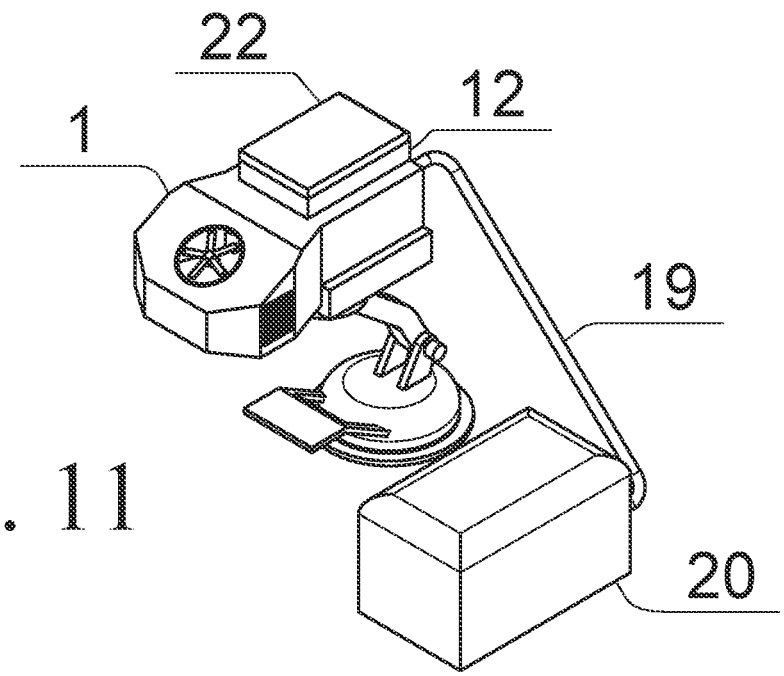
FIG. 11 is a perspective view of a preferred embodiment of a hand sanitizer, air purification, and fogger vehicle mount, having a reservoir tube that connects a refill cartridge to a reservoir.
Figure 12:
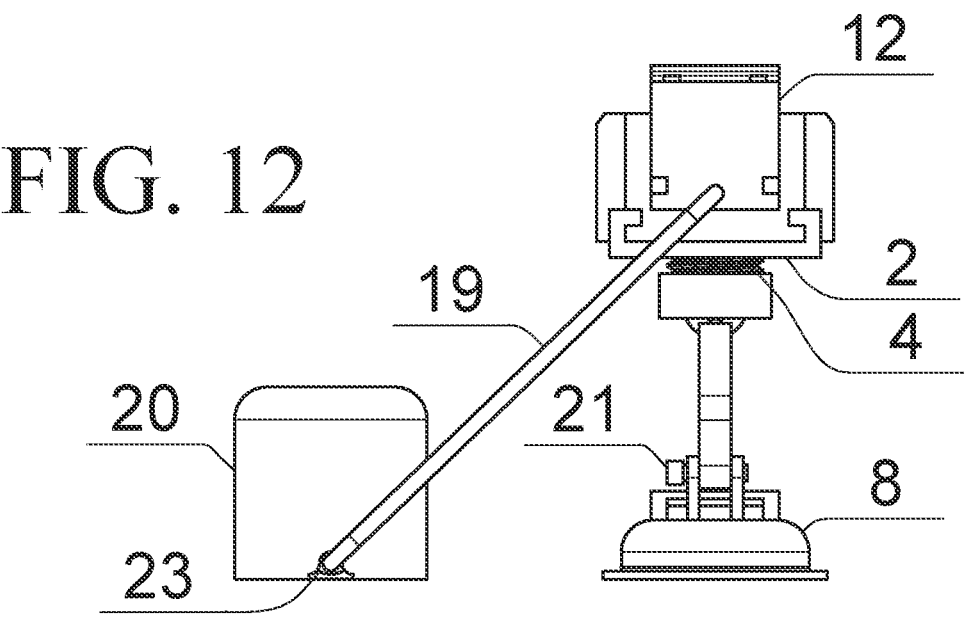
FIG. 12 is a rear view of the invention represented in FIG. 11, which illustrates a tube anchor securing a reservoir tube, so it does not dangle.
Figure 13:
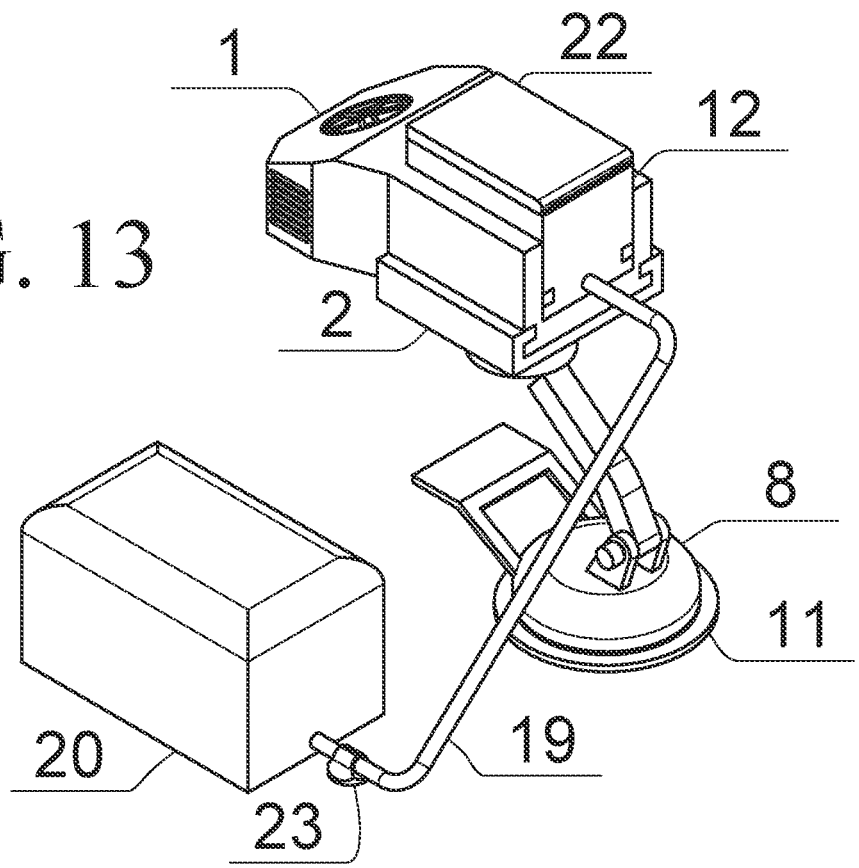
FIG. 13 is a rear perspective view of the invention represented in FIG. 11, which illustrates a tube anchor securing a reservoir tube.
Figure 14:
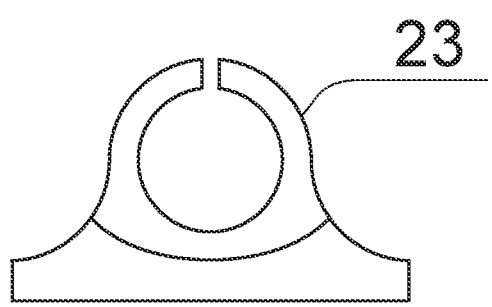
FIG. 14 is a front view of a tube anchor.
Figure 15:
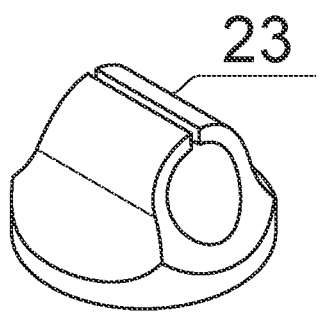
FIG. 15 is a perspective view of a tube anchor.
Figure 16:
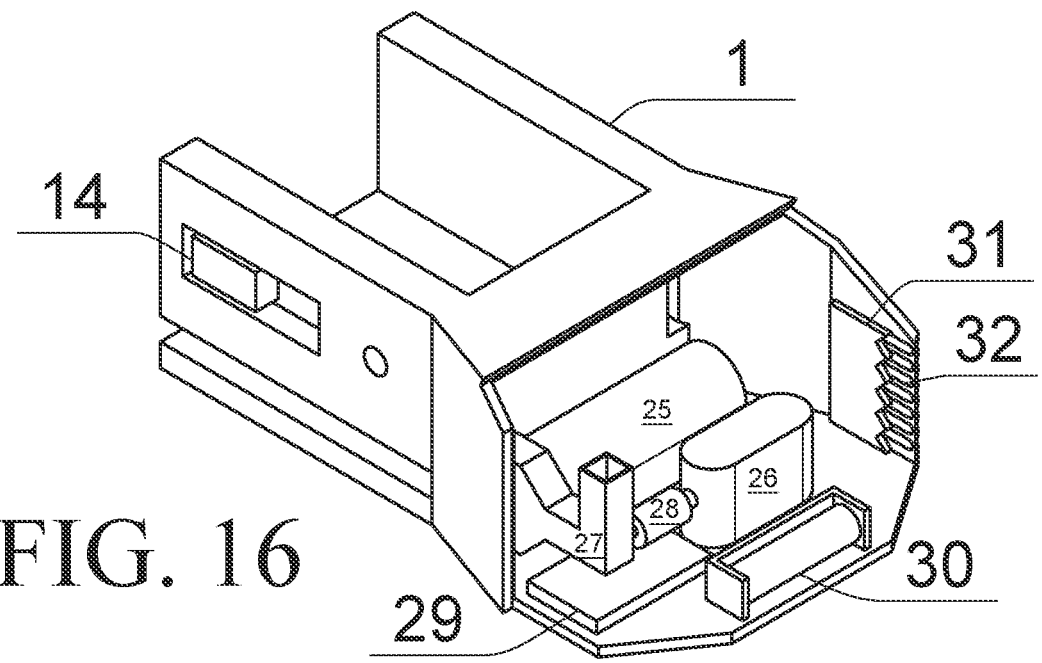
FIG. 16 is a right perspective view of the invention's mechanical elements, including vent, HEPA filter, UV lamp, duct, pump, nozzle, controller, and battery.
Figure 17:
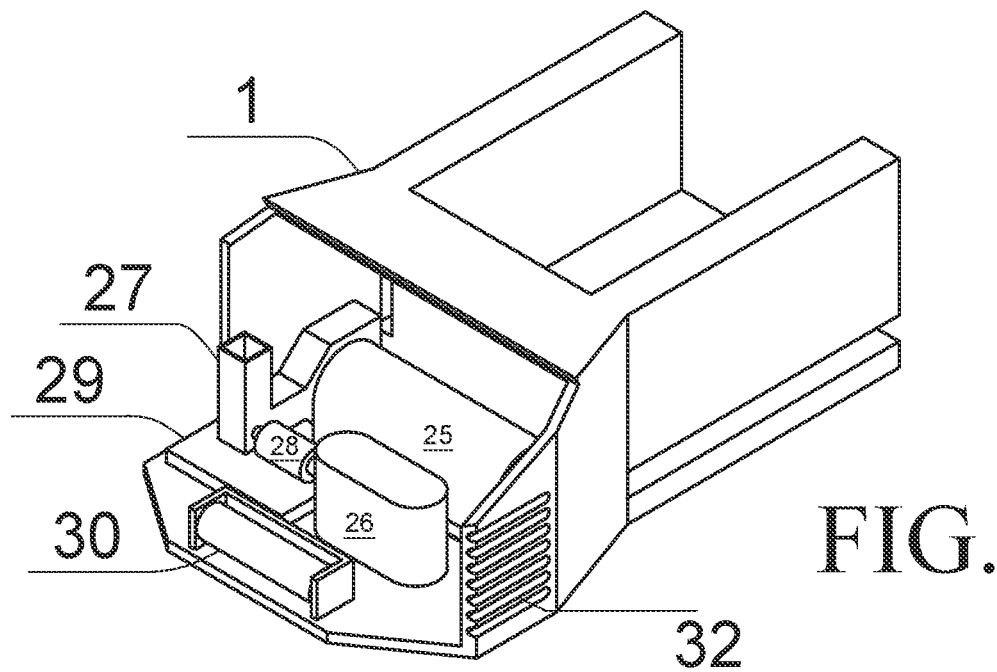
FIG. 17 is a left perspective view of the invention's mechanical elements to better illustrate the UV lamp and nozzle attachment to the duct.
Figure 18:
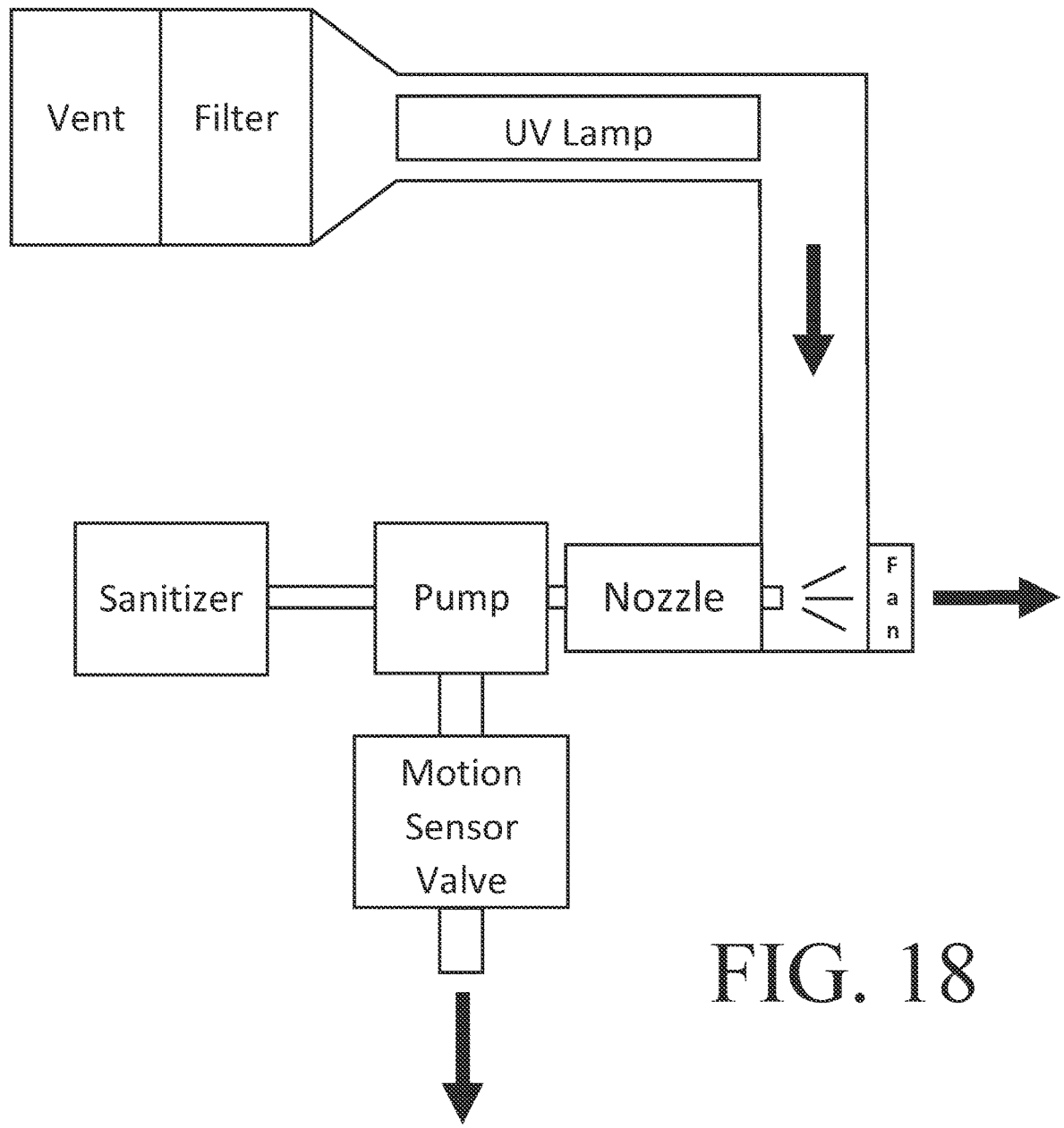
FIG. 18 is a diagram illustrating the sequential placement or operation of mechanical elements in relation to the direction of air or sanitizer flow.

The dispenser 1 has refill cartridge rails 13, which correspond with slots on a refill cartridge 12, designed to slide the refill cartridge 12 onto the dispenser 1. A refill cartridge is then locked in place. The removable refill cartridge 12 stores the hand sanitizer for the pump 26 to dispense. When the hand sanitizer from the refill cartridge 12 is emptied, the refill cartridge lock is released, to enable a new refill cartridge 12 to substitute the empty refill cartridge 12. In preferred embodiments (FIGS. 9 and 10), a refill cartridge lid 22 pivots between an open and closed configuration. The refill cartridge lid 22 enables transfer of hand sanitizer into the refill cartridge 12, making the refill cartridge reusable, cost efficient, and environmentally friendly.

The dispenser 1 has slots that correspond to rails on a mount 2. The mount 2 is removably fastened to the dispenser 1 with a mount lock 18. Because family members routinely exchange vehicles based on activities or tasks of the day, the ability to move the dispenser 1 from one vehicle to another promotes shared usage of a single device, saving money.

A ball joint socket 4 located on the bottom of the mount 2 receives an arm 7 comprising a ball joint 5. The outside wall of the ball joint socket 4 is threaded to receive a corresponding ball joint fastener 6, which secures the ball joint 5 to the ball joint socket 4. The ball joint 5 swivels to change the orientation of the dispenser 1, permitting customization of the dispenser 1 to face either a drive or passenger, based on personal preferences.

The arm 7 is attached to a base 8 with a pivot joint. The pivot joint is adjustable and lockable with an adjustable pivot bolt 21. The pivot bolt 21 modifies the overall height of the device, wherein the overall height is high enough to permit ample space for a person to place his/her hands beneath the sensor 16 and spout 17, while low enough to avoid obstructing a driver's view. In a preferred embodiment, the height of the overall device is set between 3 and 7 inches.

The base 8 houses a suction cup 10 and a lever 9, which enables the base 8 to attach to a pad 11, pneumatically. Switching the lever 9 between an upward or downward configuration modifies the air pressure inside the suction cup 10. The force generated secures the suction cup 10 to the pad 11. The pad provides a smooth flat surface for the suction cup to form a tight seal. The pad is fastened to a dashboard, holding the disperser in place on top of the dashboard of the vehicle. In a preferred embodiment, the pad fastening means is an adhesive.

The refill cartridge 12 contains a modest amount of hand sanitizer, creating a compact or sleek device. In a preferred embodiment, the refill cartridge 12 is attached to a reservoir tube 19, wherein the reservoir tube 19 connects the refill cartridge 12 to a reservoir 20. The reservoir 20 is a secondary source of hand sanitizer that continuously adds hand sanitizer to the refill cartridge 12. The reservoir 20 may be stored in a dashboard compartment, kick panel, or other storage areas within a vehicle.

The reservoir tube 19 may be cut to length. To prevent dangling, one or more tube anchor 23 secures the reservoir tube 19 to the contour of a dashboard. In a preferred embodiment, the tube anchor 23 is secured to the dashboard with adhesive, located beneath the tube anchor 23.

The air purification system utilizes a fan 24 to create negative air pressure inside the compartment housing the UV lamp 25 and duct 27 of the dispenser 1. The negative air pressure draws air through a vent 32 on a side wall of the dispenser 1. The air then moves across an air filter 31 and into a duct 27, connected to the fan 24, which discharges sterilized air.

A sterilizing fog may be added to the sterilized air. The sterilizing fog is created by withdrawing sterilizer from inside a refill cartridge 12 by a pump 26 that directs the sterilizer into a nozzle 28. In a preferred embodiment, the nozzle 28 is a fogging nozzle. In other embodiments, the nozzle 28 is a misting nozzle 28 or spraying nozzle 28. The purpose of the nozzle 28 is to create a fine layer of droplets on the surfaces (e.g., steering wheel, seats, dashboard) of the vehicle. A spraying nozzle 28 is within the scope of this invention, but the smaller micron droplet size of a fogging nozzle 28 or misting nozzle 28 is preferred. The fog or mist is pumped into the duct 27, which is carried out through the fan 24, along with the sterilized air.

Because it is anticipated the fogger operates while the vehicle is free of occupants and the vehicle is turned off, this invention has a battery 30 as an independent power source, in addition to receiving power directly from the vehicle (e.g., cigarette lighter port). A power adapter socket 15 may connected to the cigarette lighter port to either power the invention directly or recharge a battery 30 that powers the invention.

A controller 29 facilitates the logistics of operation. These include the activation of a sensor 16 that signals the pump 26 to dispense hand sterilizer. The controller 29 is also a wireless device that enables the activation of the invention remotely. In a preferred embodiment, a person may activate the fogger, air purification system, or combination thereof, after exiting the vehicle through the use of a remote device (e.g., cell phone, tablet, or computer).

The invention is made of a variety of material, which contains polymeric, ceramic, plastic, polycarbonate, metals, wood, or combination thereof. In a preferred embodiment, the material is composed with antimicrobial additives, which repel or disinfect pathogens. In a preferred embodiment, the antimicrobial additive is silver ion, zinc, copper, or ammonia compound.

It is understood that the preceding descriptions is given merely by way of illustration and various modifications may be made without departing from the scope of the invention.

I claim:

1. An apparatus to sterilize a vehicle compartment comprising:
    a dispenser, wherein the dispenser delivers sanitizer from a refill cartridge through a pump, then through a spout;
    the pump is activated by a sensor, wherein the sensor detects a person's hand proximity;
    the dispenser is removably fastened to a mount, wherein the mount is removably fastened to an arm, wherein the arm has one or more joint;
    the arm is attached to a base, wherein the base houses a suction cup that forms a removable seal with a pad, wherein the pad is secured on a dashboard of a vehicle.

2. The apparatus of claim 1, wherein the refill cartridge has a reservoir tube connected to a reservoir, wherein the reservoir tube is optionally secured by tube anchors.

3. The apparatus of claim 1, wherein the refill cartridge is removably attached to the dispenser by a mount lock.

4. The apparatus of claim 1, wherein the refill cartridge has a refill cartridge lid.

5. The apparatus in claim 1, wherein the joint of the arm is a pivot joint or a ball joint.

6. The apparatus of claim 1, wherein the suction cup forms a removable seal with the pad by actuating a lever, wherein the lever creates a negative or positive pressure beneath the suction cup.

7. The apparatus of claim 1, wherein the arm pivots relative to the base and removably locks in a desired configuration by a pivot bolt.

8. The apparatus of claim 1, wherein the dispenser receives power from a power adapter socket or a battery.

9. An apparatus to sterilize a vehicle compartment comprising:
    a dispenser, wherein the dispenser delivers sanitizer from a refill cartridge through a pump, then through a spout;
    the pump is activated by a sensor, wherein the sensor detects a person's hand proximity;

the dispenser is removably fastened to a mount, wherein the mount is removably fastened to an arm, wherein the arm has one or more joint;

the arm is attached to a base, wherein the base houses a suction cup that forms a removable seal with a pad, wherein the pad is secured on a dashboard of a vehicle;

the dispenser also disburses sanitizer through a pump, wherein the pump receives signals from a controller;

the pump connects to a nozzle, wherein the nozzle atomizes or nebulizes the sanitizer, which travels into a duct attached to a fan.

10. The apparatus of claim 9, wherein the refill cartridge has a reservoir tube connected to a reservoir, wherein the reservoir tube is optionally secured by tube anchors.

11. The apparatus of claim 9, wherein the refill cartridge is removably attached to the dispenser by a mount lock.

12. The apparatus of claim 9, wherein the refill cartridge has a refill cartridge lid.

13. The apparatus in claim 9, wherein the joint of the arm is a pivot joint or a ball joint.

14. The apparatus of claim 9, wherein the suction cup forms a removable seal with the pad by actuating a lever, wherein the lever creates a negative or positive pressure beneath the suction cup.

15. The apparatus of claim 9, wherein the arm pivots relative to the base and removably locks in a desired configuration by a pivot bolt.

16. The apparatus of claim 9, wherein the dispenser receives power from a power adapter socket or a battery.

17. The apparatus of claim 9, wherein the controller is capable of receiving a wireless signal from a device, wherein the device is a cell phone, tablet, or Wi-Fi network.

18. The apparatus of claim 9, wherein the nozzle is a fogging nozzle, misting nozzle, or spraying nozzle.

19. An apparatus to sterilize a vehicle compartment comprising:

a dispenser, wherein the dispenser delivers sanitizer from a refill cartridge through a pump, then through a spout;

the pump is activated by a sensor, wherein the sensor detects a person's hand proximity;

the dispenser is removably fastened to a mount, wherein the mount is removably fastened to an arm, wherein the arm has one or more joint;

the arm is attached to a base, wherein the base houses a suction cup that forms a removable seal with a pad, wherein the pad is secured on a dashboard of a vehicle;

the dispenser also disburses sanitizer through a pump, wherein the pump receives signals from a controller;

the pump connects to a nozzle, wherein the nozzle atomizes or nebulizes the sanitizer, which travels into a duct attached to a fan;

the dispenser has a vent, wherein air traveling across the vent passes through an air filter;

the dispenser has a UV lamp, wherein the air traveling across the UV lamp is directed into a duct, wherein the duct is attached to the fan.

20. The apparatus of claim 19, wherein the refill cartridge has a reservoir tube connected to a reservoir, wherein the reservoir tube is optionally secured by tube anchors.

21. The apparatus of claim 19, wherein the refill cartridge is removably attached to the dispenser by a mount lock.

22. The apparatus of claim 19, wherein the refill cartridge has a refill cartridge lid.

23. The apparatus in claim 19, wherein the joint of the arm is a pivot joint or a ball joint.

24. The apparatus of claim 19, wherein the suction cup forms a removable seal with the pad by actuating a lever, wherein the lever creates a negative or positive pressure beneath the suction cup.

25. The apparatus of claim 19, wherein the arm pivots relative to the base and removably locks in a desired configuration by a pivot bolt.

26. The apparatus of claim 19, wherein the dispenser receives power from a power adapter socket or a battery.

27. The apparatus of claim 19, wherein the controller is capable of receiving a wireless signal from a device, wherein the device is a cell phone, tablet, or Wi-Fi network.

28. The apparatus of claim 19, wherein the nozzle is a fogging nozzle, misting nozzle, or spraying nozzle.

29. The apparatus of claim 19, wherein the air filter is a HEPA filter.

30. The apparatus of claim 19, wherein the UV lamp radiates germicidal ultraviolet light.

31. The apparatus of claim 19, wherein the UV lamp radiates UV-C radiation.

* * * * *